(12) United States Patent
Kinosaki et al.

(10) Patent No.: US 6,399,744 B1
(45) Date of Patent: *Jun. 4, 2002

(54) TCF MUTANT

(75) Inventors: Masahiko Kinosaki, Tochigi; Kyoji Yamaguchi, Saitama; Fumie Kobayashi, Tochigi; Masaaki Goto, Tochigi; Akihiko Murakami, Tochigi; Masatsugu Ueda, Saitama; Yasushi Yamashita, Tochigi; Kanji Higashio, Saitama, all of (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/700,519

(22) PCT Filed: Dec. 27, 1995

(86) PCT No.: PCT/JP95/02708

§ 371 (c)(1),
(2), (4) Date: Aug. 26, 1996

(87) PCT Pub. No.: WO96/20214

PCT Pub. Date: Jul. 4, 1996

(30) Foreign Application Priority Data

Dec. 27, 1994 (JP) .............................................. 6-337885

(51) Int. Cl.[7] .............................................. C07K 14/00
(52) U.S. Cl. ...................... 530/350; 536/23.5; 530/333; 435/69.4; 435/240.1; 435/320.1
(58) Field of Search ............................ 435/69.4, 240.1, 435/320.1; 530/350

(56) References Cited

U.S. PATENT DOCUMENTS 5,328,836 A * 7/1994 Shima et al. ............... 435/69.4
5,648,233 A * 7/1997 Yamaguchi et al. .......... 435/69
5,714,461 A * 2/1998 Masunaga et al. .......... 435/69.1
5,998,370 A * 12/1999 Arai ............................ 424/570
6,306,827 B1 * 10/2001 Kinosaki et al. ............ 435/69.1

FOREIGN PATENT DOCUMENTS

WO          9323541       11/1993
WO    WO 9620214 A1 *     7/1996

OTHER PUBLICATIONS

Seki et al (Gene, 102:213–219), 1991.*
Burgess et al (J. Cell Bio., 111:2129–2138), 1990.*
Lazar et al (Mol. Cell Biol., 8:1247–1252), 1988.*
Tao et al (J. Immunol., 143:2595–2601), 1989.*
Bowie et al (Science, 247:1306–1310), 1990.*
Coffer et al (Biochem. J., 278:35–41), 1991.*
Higashio et al (EXS, 65:351–368), 1993.*
Shima et al (BBRC, 180:1151–1158), 1991.*
Mizuno K. et al.: "Hairpin Loop and Second Kringle Domain are Essential sites for heparin binding . . ." J. Biol. Chem., vol. 269, No. 14, Jan. 14, 1994.

* cited by examiner

Primary Examiner—Donna C. Wortman
Assistant Examiner—Stephen L. Rawlings
(74) Attorney, Agent, or Firm—Darby & Darby

(57) ABSTRACT

The present invention relates to a TCF mutant having a novel amino acid sequence which is obtained by mutagenesis of one or more amino acid between N-terminus and the first kringle of the amino acid sequence of native TCF and has lowered affinity to heparin and/or elevated biological activity. The present TCF mutant is prepared by gene manipulation of TCF. The TCF mutants of the present invention have proliferative activity and/or growth stimulative activity in hepatocyte and beneficial as a therapeutic agent for various hepatic diseases and an antitumor agent.

7 Claims, 8 Drawing Sheets

1. Reduced TCF
2. Reduced RKRR2AAAA
3. Reduced KIKTKK27AIATAA
4. Non-reduced TCF
5. Non-reduced RKRR2AAAA
6. Non-reduced KIKTKK27AIATAA

TCF MUTANT

BACKGROUND OF THE INVENTION

1. Field of the Invention

The present invention relates to TCF mutants comprising a novel amino acid sequence, more specifically, TCF mutants which are obtained by mutagenesis of one or more amino acid in the sequence from N-terminus to the first kringle of native TCF and show lowered affinity to heparin and/or elevated biological activity. The TCF mutants of the present invention which show proliferative activity and growth stimulative activity in hepatocyte are beneficial for treatment of various hepatic diseases and as an antitumor agent.

2. Background Art

Tumor cytotoxic factor (TCF-II) produced in human fibroblast cells is a novel antitumor substance different from any antitumor proteins so far reported. The present inventors have succeeded in the cloning of cDNA coding for the protein of the present invention, determined the total amino acid sequence thereof and confirmed usefulness thereof (WO90/10651). The molecular weight of TCF was 78,000±2,000, or 74,000±2,000 according to the results of SDS electrophoresis under non-reducing conditions, while the results under reducing conditions indicated A-chain of 52,000±2,000, common band, B-chain of 30,000±2,000 and/or C-chain of 26,000±2,000. TCF is a protein which has a high affinity to heparin or heparin-like substance and shows high antitumor activity against tumor cells and proliferative activity to normal cells. Further, it was confirmed that it belongs to a wide variety of family of HGF, a growth factor for hepatocyte. Therefore, since TCF is not only an antitumor factor, but also a growth factor for hepatocytes, it is known that it is beneficial for liver regeneration after hepatectomy. Much research been carried out from the aspects of structure-function relationship of hepatocyte growth factor(HGF) so far. About 20 species of deletion mutants and about 50 species of point mutants have been reported so far (K. Matsumoto, et. al., Biochem. Biophys. Res. Comm., vol. 181, pp 691–699 (1991); G. Hartmann, et. al. Proc. Natl. Acad. Sci. USA, vol. 89, pp11574–11587 (1992); N. A. Lokker, et. al., EMBO J. vol. 11, pp 2503–2510 (1992); M. Okigaki et. al., Biochemistry, vol. 31, pp 9555–9561 (1992); N. A. Locker, et. al. Protein Engineering, vol. 7, pp895–903 (1994)), however, any mutant which clearly shows an elevated biological activity has not been obtained at present. Half-life of TCF in vivo is known to be extremely short, about 2 minutes. Therefore, it is anticipated that a comparatively large amount of the protein should be administered for treatment of various diseases. It is conceivable that the dosage level of TCF administered will be reduced by elevation of biological activity thereof or by prolongation of the half-life thereof in vivo. Though it was described on TCF mutants with prolonged half-life in patent publication WO94/14845, any TCF mutant with elevated biological activity has not been obtained at present, like HGF described above.

Therefore, the present inventors have conducted an investigation to obtain a TCF mutant which shows elevated biological activity or prolongation of half-life in vivo. More specifically, the present inventors have carried out research to obtain the above-mentioned mutant with elevated biological activity or with prolonged half-life in vivo which is different from native TCF with respect to amino acid sequence by altering the DNA sequence coding for the amino acid sequence of native TCF and expressing DNA thereof. Accordingly, an object of the present invention is to provide a TCF mutant with elevated biological activity or with prolonged half-life in vivo due to lowered affinity to heparin.

The present inventors have eagerly investigated the above and obtained novel TCF mutants which have amino acid sequences different from that of TCF mutant found prior to the present invention and show elevated biological-activity and/or lowered affinity to heparin. The present invention provides TCF mutants which show more than 10 folds of specific activity (biological activity per unit amount of protein) and/or lowered affinity to heparin.

These are the first mutants with extremely elevated biological activity by mutagenizing the amino acid sequence of native TCF.

SUMMARY OF THE INVENTION

An object of the present invention is to provide a TCF mutant with lowered affinity to heparin and/or with elevated biological activity which is obtained by mutagenesis of one or more amino acid residue(s) in the amino acid sequence from N-terminus to the first kringle of native TCF.

DETAILED DESCRIPTION OF THE INVENTION AND PREFERRED EMBODIMENTS

Figure 1:
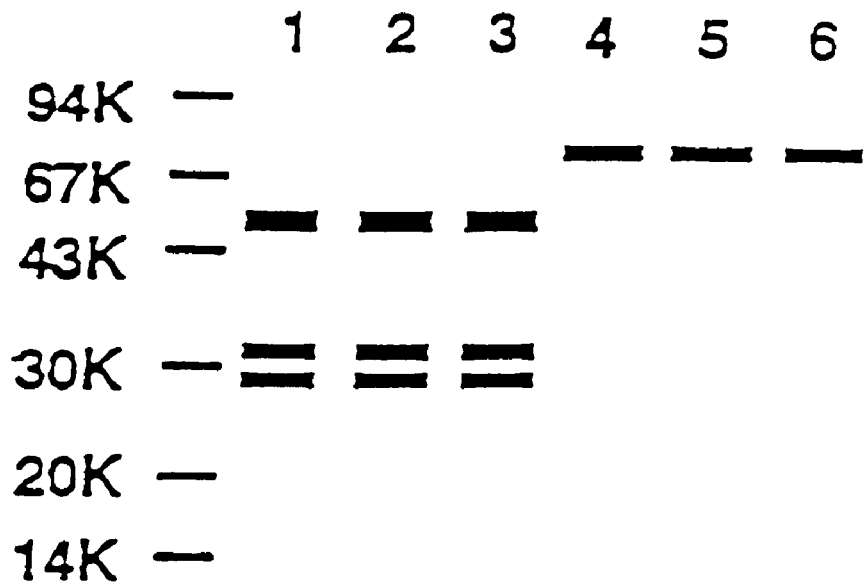
FIG. 1 shows SDS electrophoresis profiles of purified TCF and TCF mutants of the present invention

By comparing properties of native protein and a mutant obtained by mutagenesis at some portion of the amino acid sequence of the protein,function of that portion can be estimated. In the case of a protein whose structure is not clearly known, it is often used to substitute an amino acid, such as Ala, which will not affect the steric structure for a polar amino acid supposed to be on the surface of a protein to prevent a structural change of the protein due to the mutagenesis. To site-specifically change one amino-acid sequence of a protein into another, cDNA with site-specific mutations can be prepared by PCR (polymerase chain reaction) method using cDNA coding for native TCF as template and synthetic oligonucleotides coding for the other amino acids. cDNA obtained as described above can be inserted into a vector having an appropriate expression promotor (cytomegalovirus (CMV), SRa (Mole. Cell. Biol. vol. 8, No.1, pp466–472 (1988) and Japanese Published Unexamined Patent Application 277489 (1989) and transfected into eukaryotic cells, such as mammalian cells. By culturing these cells, objective TCF mutants can be prepared from the culture broth. Many TCF mutants can be constructed by introducing mutations at different sites or residues. In the present invention, 6 mutants were prepared. These mutants are specified by enumerating the amino acid sequence before mutagenesis, the number of amino acid at N-terminus of mutagenized portion and changed amino acid sequence after mutagenesis by one letter code of amino acid. For example, if the whole sequence of Arg-Lys-Arg-Arg (SEQ ID NO:20) at the second position from N-terminus is replaced with Ala, the mutant is represented as RKRR2AAAA. For another example, mutant whose original sequence Lys-Ile-lys-Thr-Lys-lys (SEQ ID NO:22) at 27th position from N-terminus is replaced with Ala-Ile-Ala-Thr-Ala-Ala (SEQ ID NO:23) is represented as KIKTKK27AIATAA (SEQ ID NO:18).

The present invention will be explained in detail by describing examples. However, these are only exemplified and the scope of the invention will not be limited by these examples.

EXAMPLE 1

Site-specific mutation was introduced by the method described below using the 6.3 kb TCF expression plasmid obtain by the method described in WO92/01053. *E. coli* comprising this plasmid was deposited as FERM BP-3479.

Deposit Agency:

National Institute of Bioscience and Human-Technology, Agency of Industrial Science and Technology, Ministry of International Trade and Industry Address:

1–3, Higashi 1 chome, Tsukuba-shi, Ibaraki-ken, Japan

Deposited on Jul. 13, 1990

I. Preparation of Template Plasmid pcD TCF001

According to the method below, a mutation was introduced at PstI cleavage site of base number 34 to change to a nucleotide sequence which could not be cleaved. PCR was carried out using 8 ng of plasmid pUC TCF (plasmid in which SalI/SphI fragment of TCF cDNA was inserted into plasmid pUC18) as a template in the presence of a combination of mutagenized primer Pst01 (Seq.ID.No.1) and a nonmutagenized primer TCF415 R (Seq.ID.No.2), and in the presence of a combination of mutagenized primer P002 (Seq.ID.No.3) and a non-mutagenized primer TCFSal-77 (Seq.ID.No.4). After the primers were removed from the reaction mixture by molecular sieving with microcon 100 (Amicon), the products were mixed. And the second PCR was carried out using primer TCFSal-77 and TCF415R. The obtained product was digested by restriction enzymes BstPI and PstI. By using a ligation kit (Takara-shuzo), the fragment was ligated with the largest Bst PI-PstI fragment of pUC TCF BstPI/PstI prepared beforehand. *E.coli* DH5α was transformed by using a part of the ligation reaction mixture. Transformed *E.coli* DH5α was cultured in L broth containing 50 µg/ml ampicillin and an objective plasmid was selected from ampicillin resistant colonies. This plasmid was digested by restriction enzymes SalI and SphI, mixed with new pcDNAI (in which multi-cloning site of pcDNAI was mutagenized and there was a HindIII-SalI-BamHI-SphI-NotI cloning site) SalI/SphI large fragment prepared beforehand and inserted by using a ligation kit. Using the reaction mixture, *E.coli* MC1061/P3 (Invitrogen) was transformed. Transformed *E.coli* MC1061/P3 was cultured in L broth containing 50 µg/ml ampicillin and 7.5 µg/ml tetracyclin.

Plasmid DNAs were prepared from obtained ampicillin-tetracyclin resistant colonies and the nucleotide sequence thereof were determined by a DNA sequencer (Perkin-Elmer). Plasmid pcD TCF001 having an objective structure was obtained and TCF mutants were prepared by using the obtained plasmid.

II. Construction of an Expression Vector for TCF Mutants and Preparation of Transformed *E.coli*.

i. Construction of RKRR2AAAA (SEQ ID NO:19) Expression-Vector and Preparation of Transformed *E.coli*.

An expression vector for cDNA coding for RKRR2AAAA (SEQ ID NO:19) was constructed by 2 steps of PCR. In the first step, a combination of mutagenized primer 2RKRRF (Seq.ID.No.5) and non-mutagenized primer TCF977 R (Seq.ID.No.6) and a combination of mutagenized primer 2RKRR R (Seq.ID.No.7) and non-mutagenized primer TCFSal-77 (Seq.ID.No.4) were used.

Four nano grams of pcD TCF001 was used as a template in both reactions. After the reactions, both reaction mixtures were admixed and purified with microcon 100. One twentieth of the mixture was used as template in the second PCR. TCFSal-77 and TCF977 R were used as primers. The reaction mixture was purified with microcon 100 and digested by restriction enzymes BstPI and EcoRV. By using the ligation kit, the fragment was inserted into the large fragment of an SRα-containing TCF expression vector cleaved by BstPI and EcoRV beforehand. *E.coli* DH5α was transformed with the ligation reaction mixture and an objective clone was obtained from the obtained ampicillin resistant cells by the same method as described. before. Plasmid DNA was prepared from the obtained clone and the DNA sequence thereof was determined by the DNA sequencer (Perkin-Elmer). And this plasmid was cleaved by restriction enzymes EcoRV and BstPI and inserted into the fragment of pUC TCF digested by restriction enzymes EcoRV and BstPI beforehand, followed by transformation of *E.coli* DH5α therewith.

*E.coli* comprising this plasmid was deposited as pUC TCF2 at National Institute of Bioscience and Human Technology on Nov. 10, 1994 and has a deposit number FERM P-14624.

ii. Construction of KIKTKK27AIATAA (SEQ ID NO:18) Expression Vector and Preparation of Transformed *E.coli*.

An expression plasmid for cDNA coding for KIKTKK27AIATAA (SEQ ID NO:8) mutant was constructed by 2 steps of PCR. In the first PCR, a combination of a mutagenized primer 27KIKTKK F (Seq.ID.No.8) and non-mutagenized primer TCF977 R (Seq.ID.No.6) and a combination of mutagenized primer 27KIKTKK R (Seq.ID.No.9) and non-mutagenized primer TCFSal-77 (Seq.ID.No.4) were used. Four ng of pcD TCF001 was used as a template in both reactions. After the reactions, both reaction mixtures were admixed and purified with microcon 100. One twentieth of the mixture was used as template in the second PCR. TCFSal-77 and TCF977 R were used as primers.

The reaction mixture was purified with microcon 100 and digested by restriction enzymes BstPI and EcoRV. By using a ligation kit, the fragment was inserted into the large fragment of the SR-α-containing TCF expression vector cleaved by BstPI and EcoRV beforehand. E.coli DH5α was transformed with the ligation reaction mixture and an objective clone was obtained from the obtained ampicillin resistant cells by the same method as described before. Plasmid DNA was prepared from the obtained clone and the DNA sequence thereof was determined by DNA sequencer. And this plasmid was cleaved by restriction enzymes EcoRV and BstPI and incorporated into a fragment of pUC TCF by digested restriction enzymes EcORV and BstPI, followed by transformation of E.coli DH5α therewith. E.coli comprising this plasmid was deposited at National Institute of Bioscience an Human-Technology Nov. 10, 1994 and has the deposit number FERM P-14623.

iii. Construction of K54A Expression Vector and Preparation of Transformed E.coli.

An expression plasmid for cDNA coding for K54A mutant was constructed by 2 steps of PCR. In the first PCR, a combination of mutagenized primer 54K F (Seq.ID.No.10) and non-mutagenized primer TCF 977 R (Seq.ID.No.6) and a combination of mutagenized primer 54K R (Seq.ID.No.11) and non-mutagenized primer TCFSal-77 (Seq.ID.No.4) were used. Four ng of pcD TCF001 was used as a template in both reactions. After the reactions, both reaction mixtures were admixed and purified with microcon 100.

One twentieth of the mixture was used as template in the second PCR. TCFSal-77 and TCF 977 R were used as primers. The reaction product was purified with microcone 100 and digested by restriction enzymes BstPI and EcORV. By using a ligation kit, the fragment was inserted into the large fragment of the SRa-containing TCF expression vector cleaved by BstPI and EcoRV beforehand. E.coli DH5α was transformed with the ligation reaction mixture and an objective clone was obtained from the obtained ampicillin resistant cells by the same method as described before. Plasmid DNA was prepared from the obtained clone and the DNA sequence thereof was determined by DNA sequencer.

iv. Construction of RGKD132AGAA Expression Vector and Preparation of Transformed E.coli.

An expression plasmid for cDNA coding for RGKD132AGAA mutant was constructed by 2 steps of PCR. In the first PCR, a combination of mutagenized primer 132RGKD F (Seq.ID.No.12) and non-mutagenized primer TCF977R (Seq.ID.No.6) and a combination of mutagenized primer 132RGKD R (Seq.ID.No.13) and primer TCF Sal-77 (Seq.ID.No.4) were used. Four ng of pcD TCF001 was used as a template in both reactions. After the reaction was through, both reaction mixtures were admixed and purified with microcon 100.

One twentieth of the mixture was used as template in the second PCR. TCFSal-77 and TCF977 R were used as primers. The reaction product was purified with microcon 100 and digested by restriction enzymes BstPI and EcoRV. By using a ligation kit, the fragment was inserted into the large fragment of the SRa-containing TCF expression vector cleaved by BstPI and EcoRV beforehand. E.coli DH5α was transformed with the ligation reaction mixture and an objective clone was obtained from the obtained ampicillin resistant cell lines. Plasmid DNA was prepared from the obtained clone in the same way as described before and the base sequence thereof was determined by DNA sequencer.

v. Construction of R142A Expression Vector and Preparation of Transformed E.coli An expression plasmid for cDNA coding for R142A mutant was constructed by 2 steps of PCR. In the first PCR, a combination of mutagenized primer 142R F (Seq.ID.No.14) and non-mutagenzed primer TCF977 R (Seq.ID.No.6) and a combination of mutagenized primer 142R R (Seq.ID.No.15) and TCFSal-77 (Seq.ID.No.4) were used. Four ng of pcD TCF was used as template in both reactions. After the reaction was through, both reaction mixtures were admixed and purified with microcon 100.

Then, one twentieth of the mixture was used as template in the second PCR. The reaction mixture was purified with microcon 100 and digested by restriction enzymes BstPI and EcoRV. By using a ligation kit, the fragment was inserted into the large fragment of the SRα-containing TCF expression vector cleaved by BstPI and EcoRV beforehand. E.coli DH5α was transformed with the ligation reaction mixture and an objective clone was obtained from the obtained ampicillin resistant cell lines in the same way as described before. The plasmid DNA was prepared from the obtained clone and the DNA sequence thereof was determined by DNA sequencer.

vi. Construction of R42A Expression Vector and Preparation of Transformed E.coli.

An expression plasmid for cDNA coding for R42A mutant was constructed by 2 steps of PCR. In the first PCR, a combination of mutagenized primer 42R F (Seq.ID.No.16) and non-mutagenized primer TCF977 R (Seq.ID.No.6) and a combination of mutagenized primer 42R R (Seq.ID.No.17) and TCFSal-77 (Seq.ID.No.4) were used. Four ng of pcD TCF001 was used as template in the both reactions. After the reaction was through, the both reaction mixtures were admixed and purified with microcon 100. One twentieth of the mixture was used as template in the second PCR. TCFSal-77 and TCF977 R were used as primers. The reaction mixture was purified with microcon 100 and was digested by restriction enzyme BstPI/EcoRV. By using a ligation kit, the fragment was inserted into the large fragment of the SRα-containing TCF expression vector cleaved by BstPI and EcoRV beforehand. E.coli DH5α was transformed with the ligation reaction mixture and an objective clone was obtained from ampicillin resistant cell lines in the same way as described before. The plasmid DNA was prepared from the obtained clone and the DNA sequence thereof was determined by DNA sequencer.

III. Preparation and Purification of Expression Plasmids for TCF Mutants

Six species of transformed E.coli comprising the above expression plasmids were cultured in L broth (400 ml) containing 50 μg/ml ampicillin in a shaking incubator at 37° C. overnight, wherein Spectinomycin (Sigma) was added up to a final concentration of 0.3 mg/ml when OD600 of cultured broth became 1.0. According to the method of Maniatis (Molecular cloning 2nd ed. pp1.21–1.52 (1989), Cold Spring Harbor Laboratory), plasmid DNA was isolated by alkaline SDS method and 6 species of TCF mutan expression plasmids were purified by cesium density gradient centrifugation method.

IV. Transfection of TCF Mutant Expression Plasmid into Animal Cell.

All the mutant expression plasmids were transfected into Chinese Hamster Ovary cell. CHO cells ($2 \times 10^6$) were suspended in 0.8 ml IMDM medium (Gibco) containing 10% fetal calf serum (FCS) (Gibco), in which a solution of 200

μg of expression vector and 10 μg of Blasticidin resistant gene expression plasmid pSV2 bsr (Funakoshi) dissolved beforehand in 25 μl of TE (10 mM Tris-HCl (pH8.0)-1 mM EDTA) was further suspended. This suspension received electroporation under the conditions of 330V and 960 μF. After leaving it at room temperature for 10 minutes, it was suspended in 10 ml of the IMDM medium and cultured at 37° C. in a $CO_2$ incubator (5 $CO_2$) for 2 days. Two days after, the supernatant was collected and the amount of the expressed TCF mutant was analyzed by enzyme immunoassay (EIA) (N. Shima, et. al., Gastro-enterologia Japonica, Vol. 26, No. 4. pp477–482 (1991)) using anti-TCF monoclonal antibody. It was used as a sample for assaying biological activity. The cells were harvested from the bottom of flasks by trypsin (Gibco) treatment and the number of viable cells was counted. About 10,000 cells/well were placed in 96-well plates(Nunc) and cultured in 200 μl/well selective of the IMDM medium containing 5 μg/ml Blastcidine for 2–3 weeks. 2–3 weeks after, 50 μl aliquot was taken from each well and investigated on the expression of TCF mutant by EIA. Cell clones expressing the TCF mutants were grown in 12-well plates and 25 $cm^2$ flasks. The cell lines producing TCF mutant were established from CHO cells by the above operation.

V. Large Scale Cultivation of TCF Mutant Producing Cells

Mutant producing cells were harvested from 75 $cm^2$ flasks by trypsin treatment when it became confluent and those cells were transferred into 10 225 $cm^2$ flasks containing 100 ml of the medium and cultured for a week. Then the cultured supernatant was collected. By repeating this operation once or twice times, 1–2 1 of the cultured broth was obtained.

VI. Purification of the TCF mutants

It was purified by 3 steps as described below.

i. Heparin-Sepharose CL-6B

Precipitates were removed from one-two liter of cultured medium of CHO cells expressing each TCF mutant by centrifugation (2,000 rpm×10 min.) of the medium and filt filtration the supernatant through a 0.45 μm filter (German Science). TCF mutant was adsorbed at 4 ml/min. on a heparin-Sepharose CL-6B column (25 mm ×120 mm, pharmacia) equilibrated with 10 mM Tris-HCl (pH 7.5) containing 0.3M NaCl and 0.01% Tween 20. The column was washed with about 500 ml of equilibration buffer and the TCF mutant was eluted by 10 mM Tris-HCl (pH 7.5) containing 2M NaCl and 0.01% Tween 20. The eluted solution was fractionated to 4 ml each by a fraction collector and the fractions having absorption at 280 nm were collected.

ii. Mono S FPLC

The fraction containing TCF mutant eluted with 2M NaCl was dialyzed against 10 mM phosphate buffer (pH 7.0) containing 0.15M NaCl, followed by centrifugation (12,000 rpm×90 min.) to remove precipitate. The supernatant containing TCF mutant was passed through on a Mono S column (5 mm×50 mm, Pharmacia) equilibrated with 10 mM phosphate buffer (pH 7.0) containing 0.15 M NaCl and 0.01% Tween 20 at flow rate of 1 ml/min. for TCF mutant to be adsorbed thereon. After the column was washed with about 30 ml of equilibration buffer, TCF mutant was eluted ,by changing the flow rate to 0.5 ml/min, with a linear gradient of NaCl up to 1.0 M for 60 min. The eluted solution was fractionated to 5 ml each by a fraction collector and fractions containing TCF mutant was analyzed by absorption at 280 nm and EIA and collected.

iii. Heparin 5-PW FPLC

To the fraction containing TCF mutant obtained using Mono S column chromatography 2-fold amount of 10 mM Tris-HCl (pH 7.5) containing 0.01% Tween 20 was added. The solution was passed through a Heparin 5-PW column (5 mm×75 mm TOSOH) 1 ml/min. equilibrated with 10 mM Tris-HCl (pH 7.5) containing 0.3M NaCl and 0.01% Tween 20 for TCF mutant to be absorbed thereon. By changing the flow rate to 0.5 ml/min., TCF mutant was eluted with a linear gradient of NaCl up to 2.0 M for 60 min.

The eluted solution was fractionated to 5 ml each by a fraction collector. The fraction containing TCF mutant was analyzed by 280 nm absorption and EIA and collected. The obtained TCF mutant solution was dialyzed against PBS containing 0.01% of Tween 20 (TPBS) so as to be the final purified product. The amount of protein in the final purified product was determined by Lowry method. The amino acid sequence of TCF mutant RKRR2AAAA and that of mutant KIKTKK27 were represented in Seq.ID.No.18 and in Seq.ID.No.19 respectively.

VII. SDS-polyacrylamide Gel Electrophoresis of Purified TCF Mutant

Purified TCF mutant (200 ng) was applied on SDS polyacrylamide gel electrophoresis. Schematic representation of electrophoresis of TCF mutant RKRR2AAAA and KIKTKKK27AIATAA (SEQ ID NO:18), which exhibited 10-fold increase in biological activity as described below, and native TCF was shown in FIG. 1. Both of the results under reducing conditions(in the presence of β-mercaptoethanol) and non-reducing conditions (in the absence of β-mercaptoethanol) did not show any difference among the three. In addition, there was no band but those to be expected from the structure of both TCF mutants.

EXAMPLE 2

Affinity of TCF and TCF Mutant to Heparin

I. Heparin-Sepharose CL-6B

Precipitates were removed from the cultured medium of CHO cells expressing each TCF mutant by centrifugation (1,200 g×10 min.) of the medium and by filtrating the supernatant through a 0.22 m filter. The filtrated supernatant was charged on a Heparin-Sepharose CL-6B column (5mm×5 mm; Pharmacia) equilibrated with TPBS for TCF mutant to be adsorbed thereon. After washing with 3 ml TPBS, TCF mutant was eluted with 1 ml of TPBS containing 0.2–0.3M NaCl, increasing the salt concentration stepwise. The concentration of TCF mutant in the eluate was analyzed by EIA and the salt concentration of the eluate was defined as affinity of mutant to heparin.

II. Heparin 5-PW FPLC

The cultured broth of CHO cells expressing each TCF mutant (30–60 ml) was centrifuged (1,000 g×10 min.), passed through 0.22 μm filter to remove precipitate and applied on a Heparin 5-PW column equilibrate with 20 mM Tris-HCl buffer solution containing 0.01% Tween 20 at a flow rate of 1.0 ml/min. for TCF mutant to be adsorbed. After washing the column with about 20 ml of equilibration buffer solution and changing the flow rate to 0.5 ml/min., TCF mutant was eluted with a linear gradient of NaCl up to 1.5 M for 45 minutes. Fractions of 0.5 ml each were taken by a fraction collector and the concentration of TCF mutant in each fraction was quantified by EIA and the salt concentration of the elution was defined as affinity of mutant to heparin.

The results of determination of affinity of these TCF mutant to heparin are shown in table 1. The elution concentration of NaCl from heparin-Sepharose represents the concentration at which TCF mutant is eluted in the maximum amount. The relative ratio of elution concentration is defined as (the elution concentration of NaCl of mutant TCF/that of native TCF). And n.d. means "not determined". In the examination with heparin-Sepharose, RKRR2AAAA (SEQ ID No:19), KIKTKK27AIATAA (SEQ ID No:18), and R42A exhibited significantly lowered affinity to heparin. Further, in the examination with heparin 5-PW, it was observed that affinity of the mutants to heparin was lowered to around 70% of that of native TCF.

TABLE 1

| | Example 3 | | |
|---|---|---|---|
| | Heparin-Sepharose Elution Concentration of NaCl(M) | Heparin 5-PW Elution Concentration of NaCl(M) | Relative Ratio of Elution concentration |
| TCF | 0.9 | 1.14 | 1.00 |
| RKRR2AAAA (SEQ ID NO: 19) | 0.6 | 0.78 | 0.68 |
| KIKTKK27AIATAA (SEQ ID NO: 18) | 0.6 | 0.82 | 0.72 |
| R42A | 0.7 | 0.84 | 0.74 |
| K54A | 0.9 | 1.10 | 0.96 |
| RGKD132AGAA | 0.9 | n.d. | n.d. |
| R142A | 0.9 | n.d. | n.d. |

EXAMPLE 3

Proliferative Activity of TCF and TCF Mutants on Hepatocyte in vitro

Figure 2:
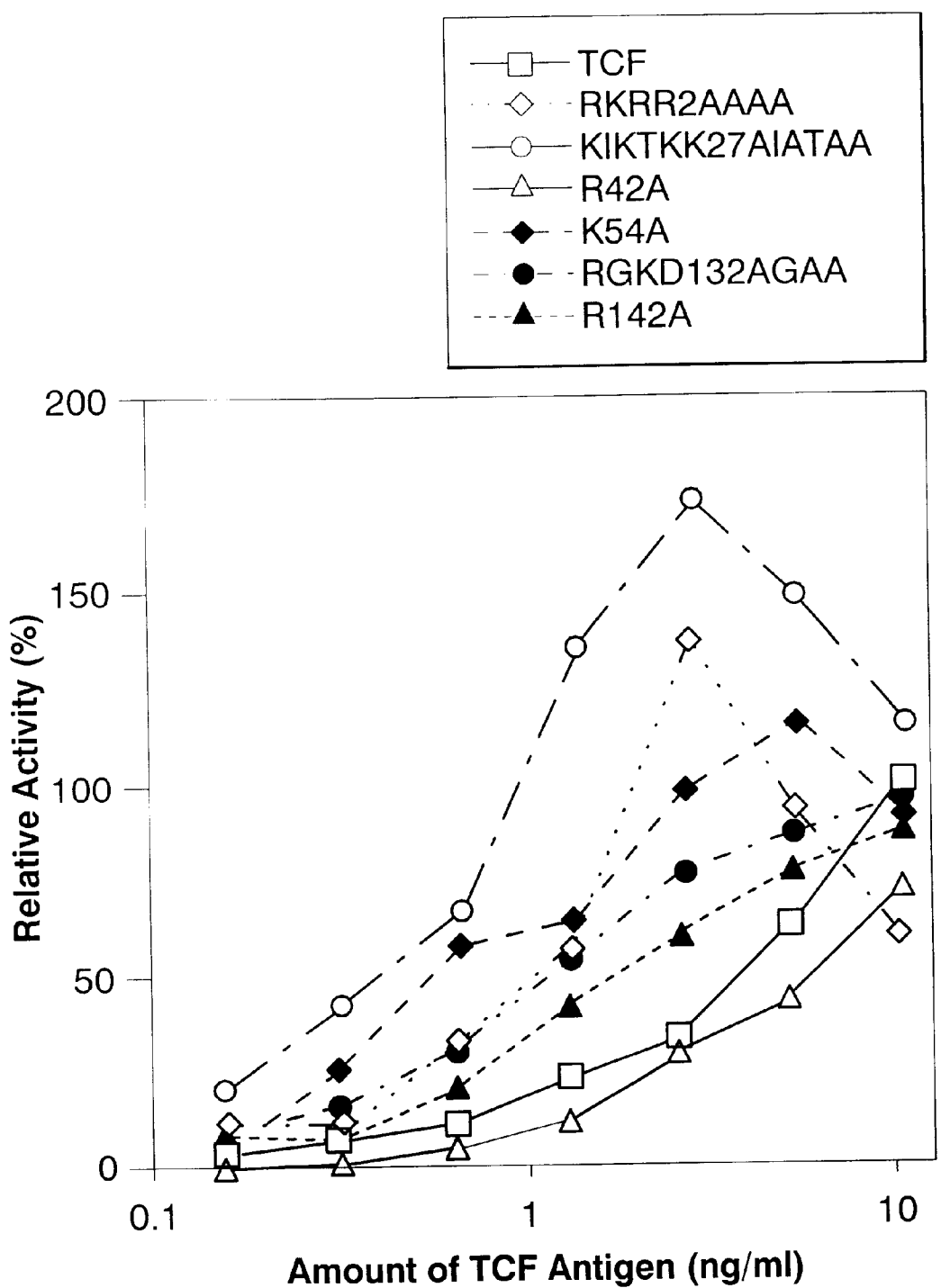
FIG. 2 is a graph showing the proliferative action of purified TCF and TCF mutants of the present invention in hepatocyte. The relative activity (%) of vertical axis is represented as the ratio of proliferative activity of each sample based on that of 10 ng/ml TCF as 100%.
Figure 3:
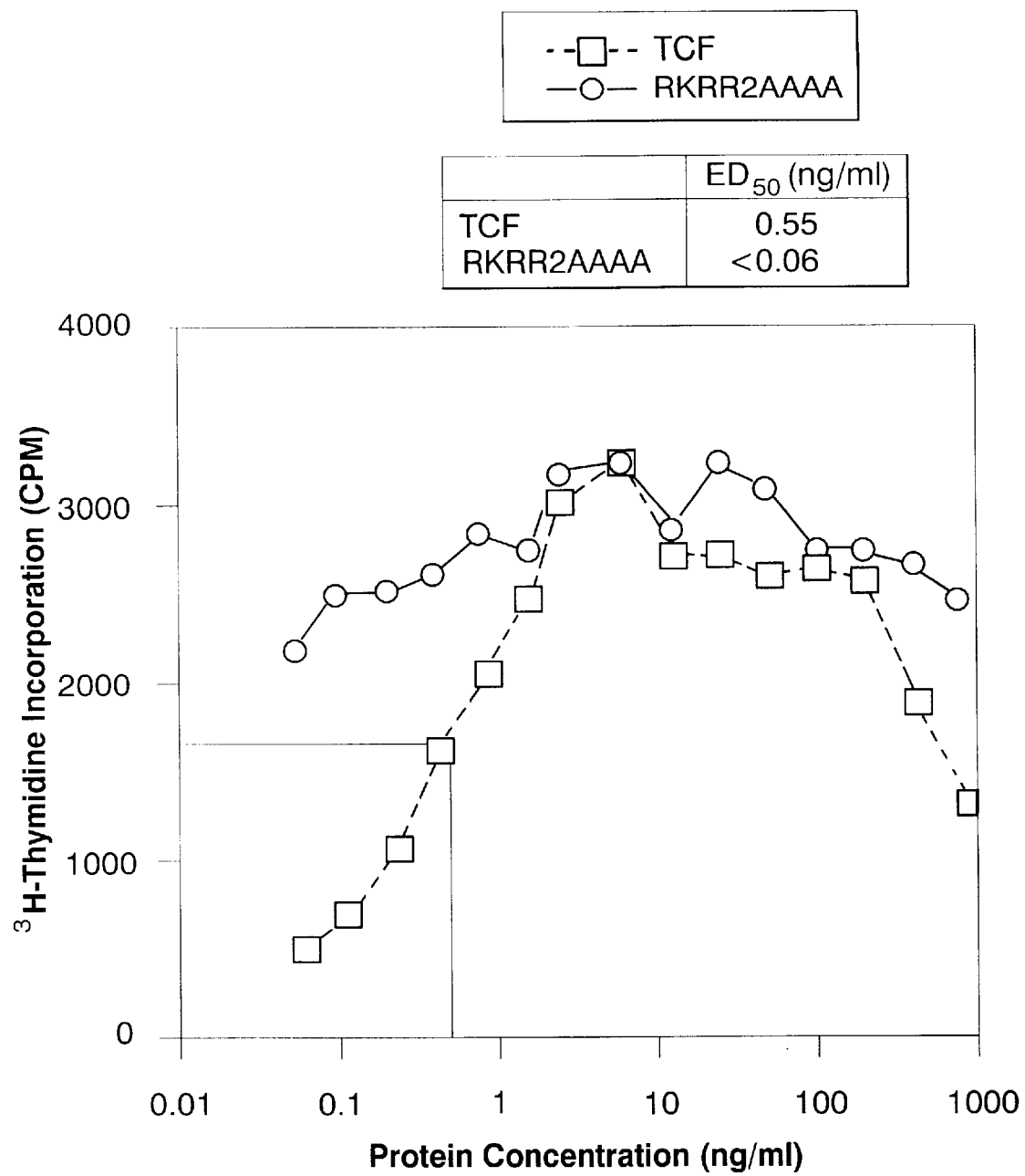
FIG. 3 is a graph showing the comparison of proliferative action in hepatocytes between purified mutant RKRR2AAAA (SEQ ID NO:19) and TCF.
Figure 4:
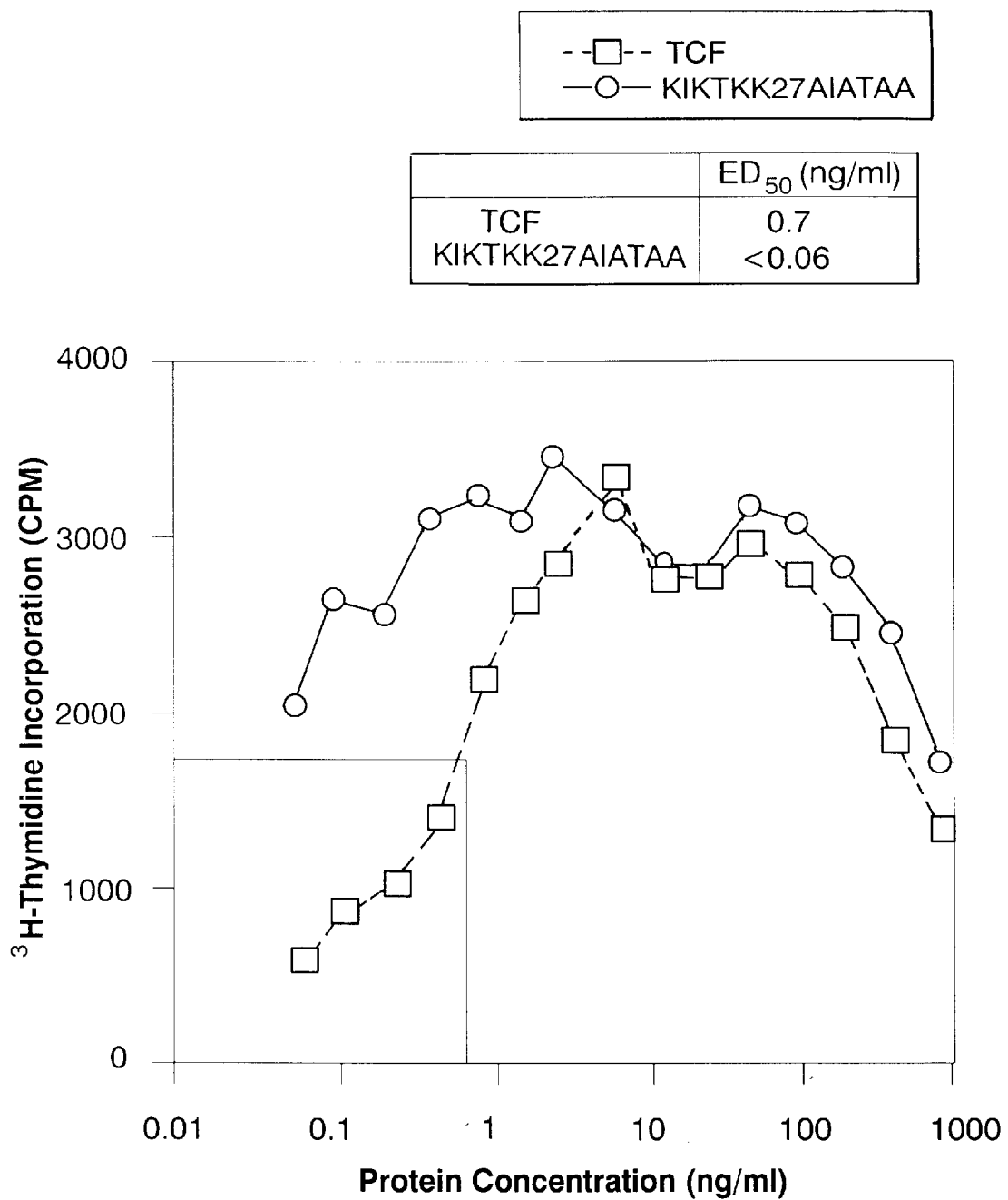
FIG. 4 depicts comparison of proliferative action in hepatocytes between purified mutant KIKTKK27AIATAA (SEQ ID NO:18) and TCF.

Proliferative activity was investigated by the following method:

According to the method of Segren (Method in cell biology, Vol. 13, p29 (1976) Academic Press, New York), hepatocyte was isolated from Wister rats (about 200 g of body weight). The cells ($1.0 \times 10^4/50$ µl/well) were placed into the wells of 96-wellplate (Falcon) and cultured at 37° C. overnight using Williams E medium (Flow Laboratory) containing 10% fetal calf serum and 10 µM dexamethasone (hereinafter, abbreviated as base medium). After 24 hours, 10 µl of base medium containing TCF or TCF mutant was added to each well. The plates were incubated at 37° C. for another 22 hours. After 22 hours, $^3$H-thymidine (Amersham) was added thereto so as to be 1 µCi/well, keeping the culture another 2 hours. After then,the cells were washed twice with PBS and harvested by treatment of 5% trypsin followed by collection of the cells in a glass filter by cell harvester. The radio activity incorporated in each well was measured by Matrix 96 (Packard) as the amount of DNA synthesis. The results are shown in FIG. 2. When biological activities at 2.5 ng/ml TCF antigen, mutant K54A had about 1.4-fold increased biological activity, RGKD 132 AGAA about 2.0-fold the amount of purified protein of mutants with lowered affinity to heparin was determined by Lowery method and the biological activities were compared with regard to the amount of protein exhibiting 50% of maximum proliferative activity (ED50) (FIGS. 3 and 4). As the results, 2 species of protein, that is, RKRR2AAAA (SEQ ID No:19) and KIKTKK27AIATAA (SEQ ID No:18), exhibited more than 10 folds of biological activity per unit amount of protein comparing with that of native TCF.

EXAMPLE 4

Proliferative Activity of TCF and TCF Mutant in Kidney Epithelial Cells

Figure 5:
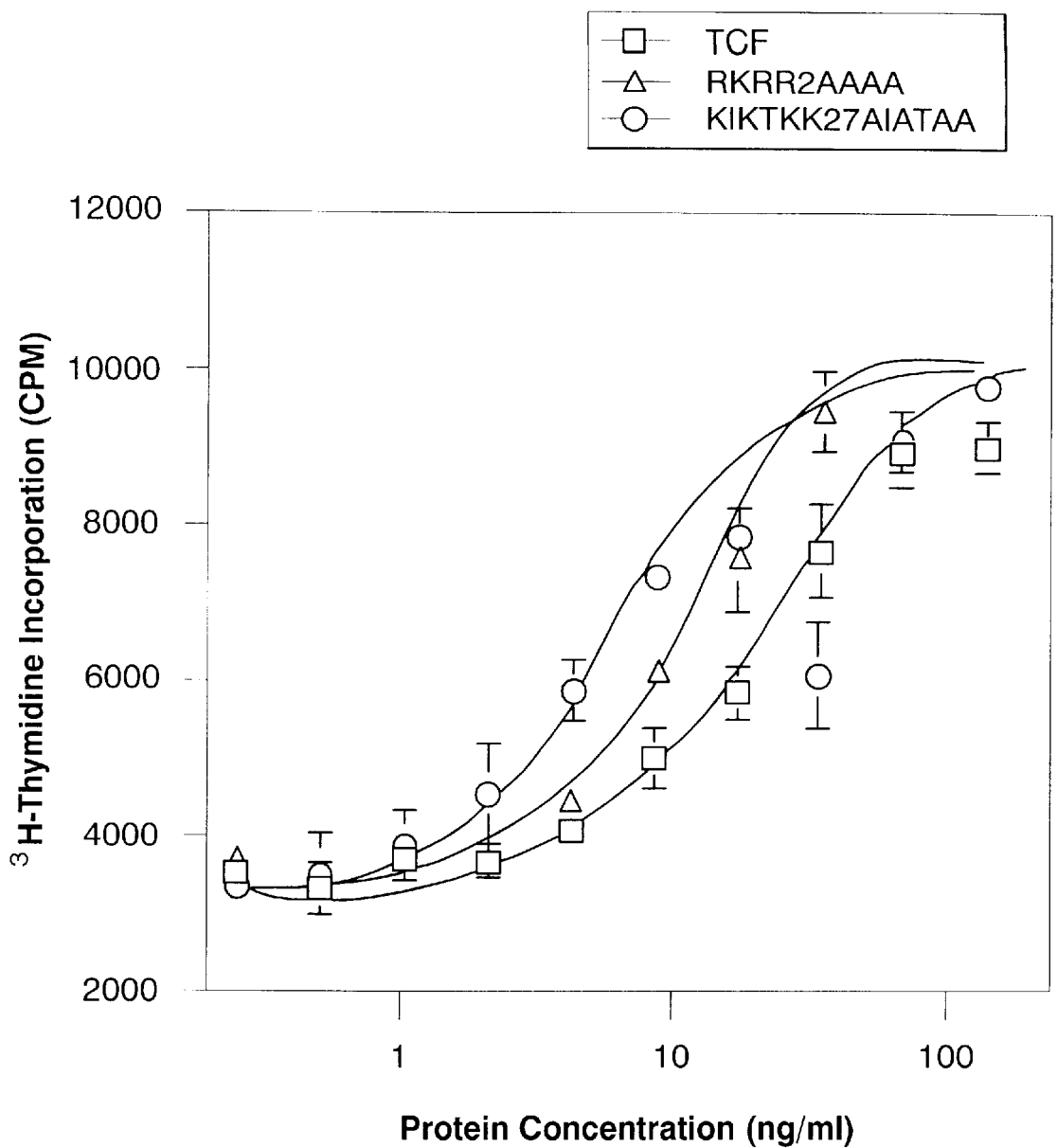
FIG. 5 in graph from a comparison of proliferative action in kidney epithelial cells among purified mutant RKRR2AAAA (SEQ ID NO:19), mutant KIKTKK27AIATAA (SEQ ID NO:18) and TCF.

Proliferative Activity in Kidney Epithelial Cell was Determined by the Following Method:

OK cells derived from kidney epithelial cell line of American Opossum were placed into each well of 96 well-plate so as to be $1.0 \times 10^4/100$ µl/well and cultured in DMEM medium containing 10% fetal calf serum at 37° C. overnight. After then, each well was washed 2–3 times with DMEM medium containing no serum. The medium in each well was replaced with DMEM medium containing no serum and culture was kept at 37° C. for another 2 days. Then, the medium in each well was again replaced with 50 µl of fresh DMEM medium containing no serum and, with 50 µl of addition of TCF or TCF mutant diluted with DMED medium containing 0.2% bovine serum albumin, cultur was kept for another 24 hours. After 24 hours, $^3$H-thymidine was added thereto so as to be 1 µCi/well and the culture was kept for another 2 hours. Then, cells were washed with PBS twice and the cells were harvested by treatment of 0.5% trypsin, followed by collection of the cells in a glassfilter by a cell harvester. The radio activity incorporated in each well was measured by Matrix 96 and determined as the amount of DNA synthesis. The results were exhibited in FIG. 5.

As the results,it was observed that biological activities per unit amount of protein of RKRR2AAAA (SEQ ID No:19) and KIKTKK27AIATAA (SEQ ID No:18) in kidney epithelial cell increased more than 2 folds comparing with that of native TCF.

EXAMPLE 5

Proliferative Activity of TCF and TCF Mutant in Bone Marrow Cell in vitro

Proliferative Activity in Bone Marrow Cell was Determined by the Following Method:

NFS-60 cells which are from a mouse bone marrow cell line were placed into each well of 96 well-plate spas so be $5.0 \times 10^4$ cells/50 µl/well in RPMI medium containing 10% fetal calf serum and, with addition of 50 µl of TCF or TCF mutant diluted with the medium, cultured at 37° C. for 24 hours. After 24 hours, 10 µl of 5 mg/ml MTT (Sigma) was added to each well and the culture was kept for another 4 hours. Then, 100 µl of 10% SDS/10 mM ammonium chloride was added to each well and it was left at room temperature overnight. After that, optical absorbance at 590 nm was measured by Immunoreader NJ-2000 (Intermed) as proliferative activity.

Figure 6:
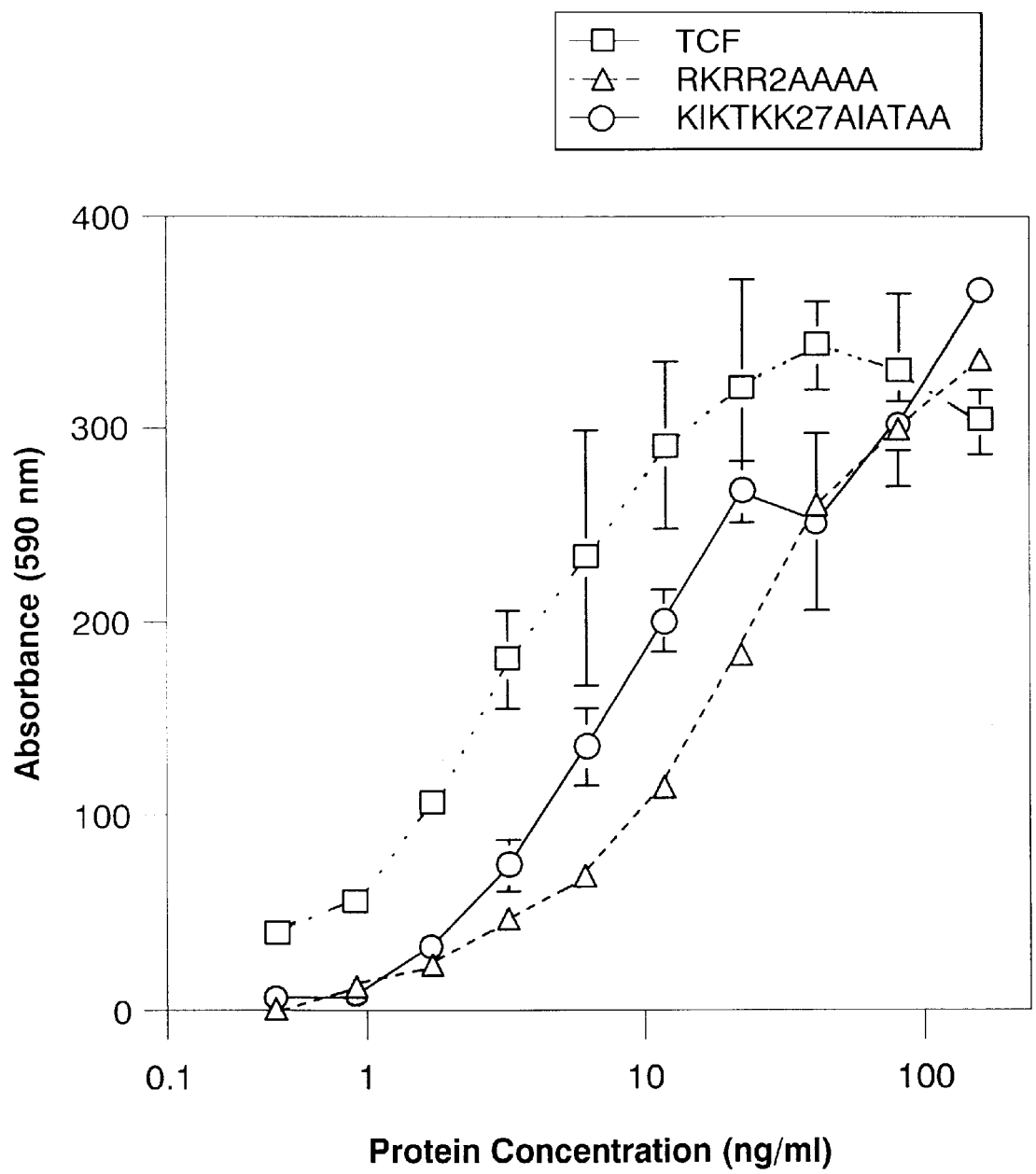
FIG. 6 also in graph from shows the comparison of proliferative action in bone marrow cells among purified mutant RKRR2AAAA (SEQ ID NO:19), mutant KIKTKK27AIATAA (SEQ ID NO:18) and TCF.

The results were exhibited in FIG. 6. As the results, it was observed that biological activities per unit amount of protein of RKRR2AAAA (SEQ ID No:19) and KIKTKK27AIATAA (SEQ ID No:18) in bone marrow cell decrease to ½–1/20 of that of native TCF.

EXAMPLE 6

In vivo Biological Activity of TCF and TCF Mutants

In vivo Biological Activity was Assayed by the Following Method:

TCF or TCF mutant dissolved in PBS containing 0.01% Tween 20 was intravenously administered through tail (2 ml/Kg×2 times/day) in 6 weeks old male Wister rats for 4 days. At the next day to the final administration, blood samples were taken from caudal vena cava under ether anesthesia and serum thereof were collected by centrifugation (3000 rpm×10 min.) and, in the case of plasma, immediately after sampling blood, sodium citrate (the final concentration was 0.38%) was added thereto followed by centrifugation(3000 rpm×10 min.) to give plasma. After serum or plasma obtained was preserved in a freezer kept at +30° C., serum level of total protein, albumin, unsaturated iron binding capacity, total cholesterol, free cholesterol, HDL-cholesterol and phospholipid were analyzed by serum autoanalyzer (Hitachi 7150 Autoanalyzer) and plasma level of prothrombin time and fibrinogen were analyzed by Auto blood coagulation analyzer KC40 (Amerung). For these analysis, the following analyzing kits were used:

Total protein: Autosera$^{TR}$ TP, Albumin: Autosera$^{TR}$ ALB, Unsaturated iron-binding capacity: Clinimate$^{TR}$ UIBC, Total cholesterol: Autosera$^{TR}$ CHO-2, Free cholesterol: Autosera$^{TR}$ F-CHO-2, HDL-cholesterol: HDL-C-2 "DAIICHI", Phospholipid: Autosera$^{TR}$ PL-2, (All the above kits were products of Daiichi-Pure Chemicals Co., Ltd.)

Figure 7:
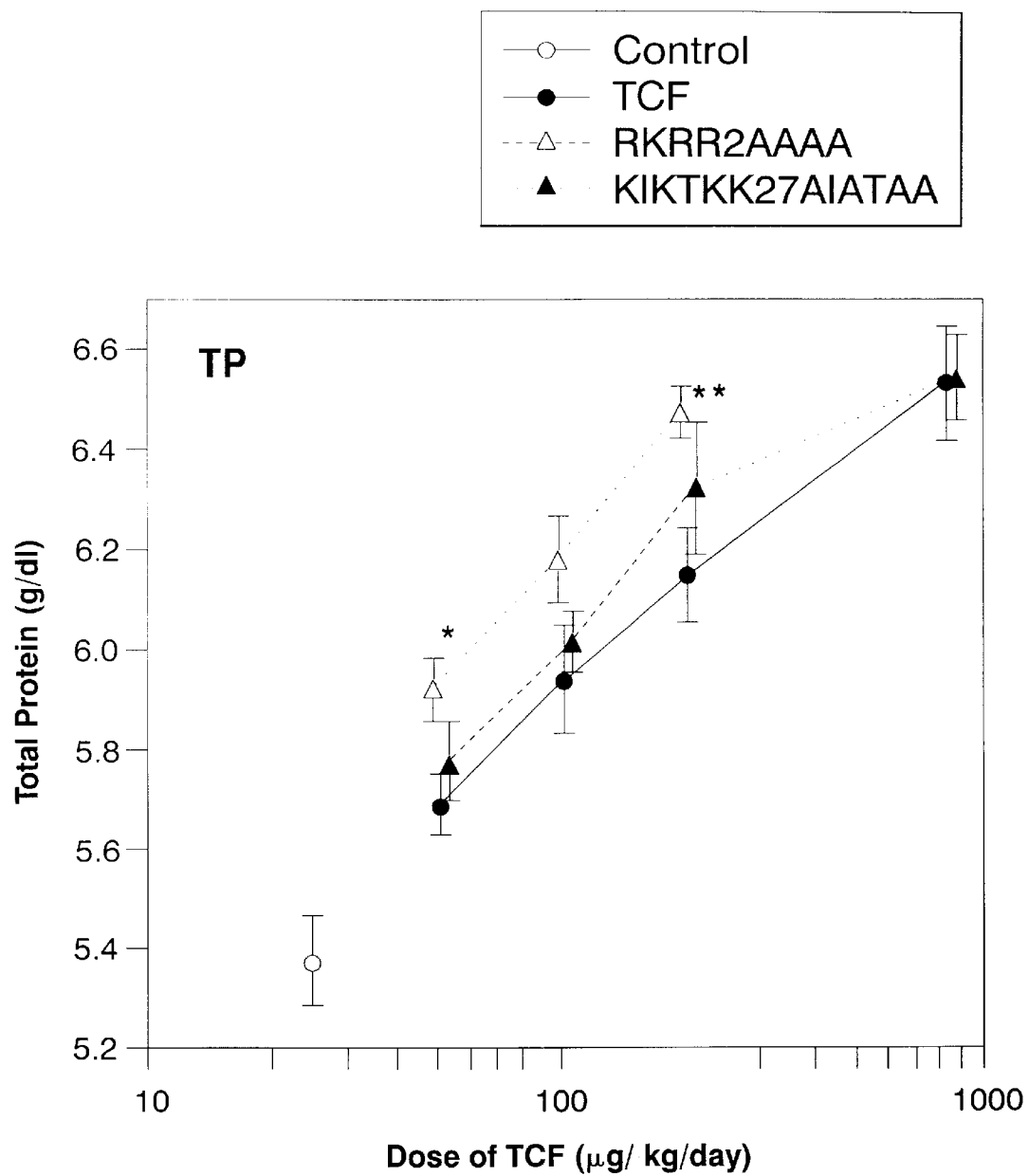
FIG. 7 shows dose effects of purified TCF, mutant RKRR2AAAA (SEQ ID NO:19) and mutant KIKTKK27AIATAA (SEQ ID NO:18) on the serum level of total protein in rats.
Figure 8:
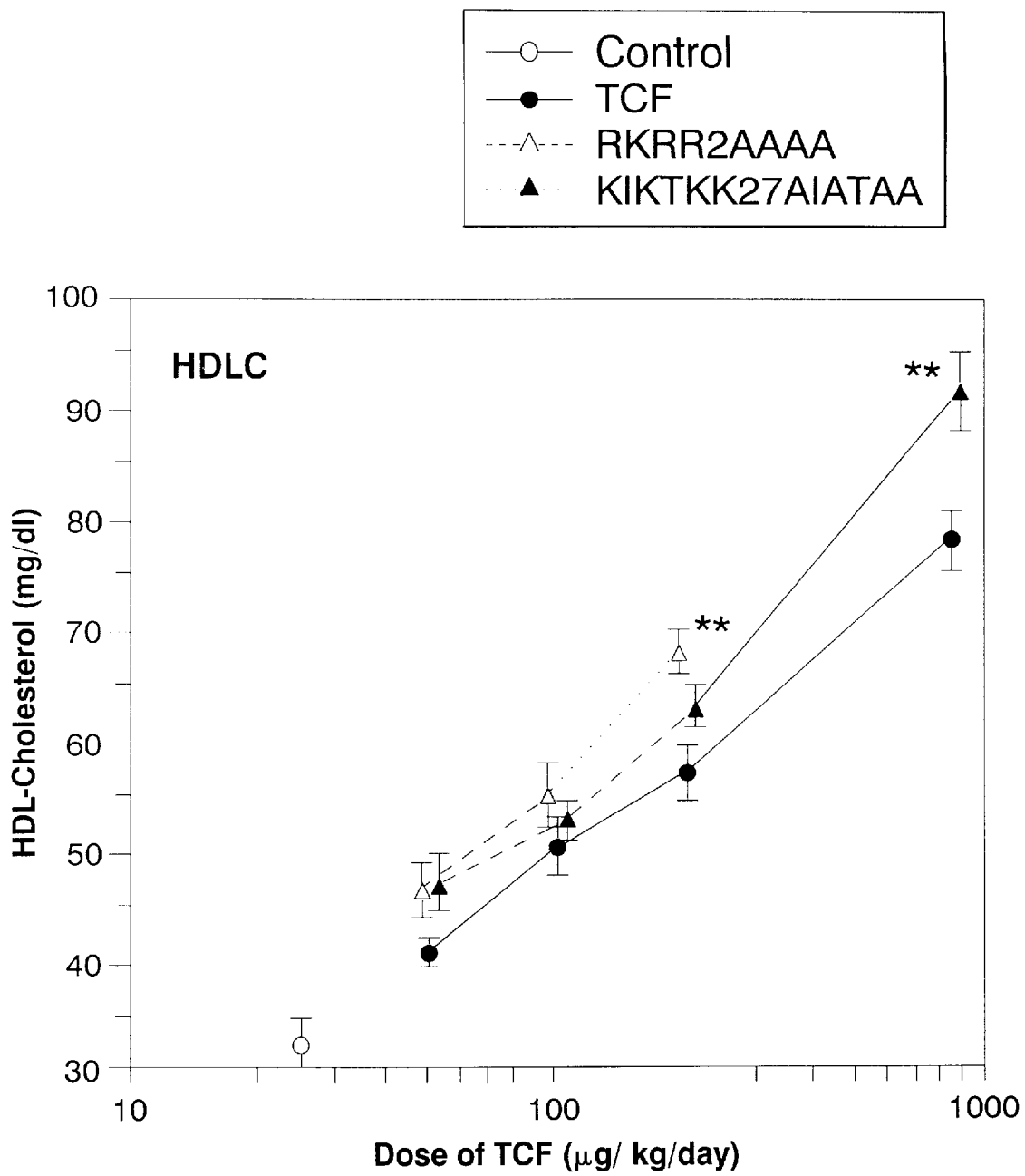
FIG. 8 in graph from the dose effects of purified TCF, mutant RKRR2AAAA (SEQ ID NO:19) and mutant KIKTKK27AIATAA (SEQ ID NO:18) on the serum level of HDL-cholesterol in rats.

Prothrombin time: Orthobrain thromboplastin (Ortho Diagnostic System Inc.), Fibrinogen: Sun assay Fib (Nitto Boseki Co., Ltd.). As typical examples, dose effects thereof on serum level of total protein and on serum level of HDL-cholesterol were exemplified in FIG. 7 and FIG. 8 respectively. According to the results of statistical analysis of parallel line assay, with respect to increase of total protein, RKRR2AAAA (SEQ ID No:19) exhibited 2.12 folds of specific activity and KIKIKTKK27AIATAA (SEQ ID No:18) exhibited 1.37 folds of specific activity, comparing to that of native one. Further, with respect to increase HDL-cholesterol, RKRR2AAAA (SEQ ID No:19) exhibited 1.66 folds of specific activity and KIKTKK27AIATAA (SEQ ID No:18) exhibited 1.62 folds of specific activity, comparing to that of native one.

Industrial Availabilities

The present invention provides a novel TCF mutant. The TCF mutant of the present invention has proliferative activity and growth stimulative activity in hepatocyte and is beneficial for treatment of various hepatic diseases and as an antitumor agent.

We claim:

1. A tumor cytotoxic factor (TCF) mutant which is obtained by mutagenesis of one or more than one amino acid residue of the amino acid sequence of native TCF of the expression plasmid deposited under Accession Number FERM BP-3479, said mutant being selected from the group consisting of:
   (a) the mutant of SEQ ID NO: 18;
   (b) the mutant of SEQ ID NO: 19;
   (c) the mutant wherein Lys54 of said amino acid sequence of native TCF is mutagenized to Ala;
   (d) the mutant wherein Arg132-Gly-Lys-Asp135 (SEQ. ID NO: 24) of said amino acid sequence of native TCF is mutagenized to Ala-Gly-Ala-Ala (SEQ. ID NO: 25);
   (e) the mutant wherein Arg142 of said amino acid sequence of native TCF is mutagenized to Ala;
   (f) the mutant wherein Arg42 of said amino acid sequence of native TCF is mutagenized to Ala.

2. The TCF mutant according to claim 1, wherein Lys54 of said amino acid sequence of native TCF is mutagenized to Ala.

3. The TCF mutant according to claim 1, wherein Arg132-Gly-Lys-Asp135 (SEQ. ID NO: 24) of said amino acid sequence of native TCF is mutagenized to Ala-Gly-Ala-Ala (SEQ. ID NO: 25).

4. The TCF mutant according to claim 1, wherein Arg142 of said amino acid sequence of native TCF is mutagenized to Ala.

5. The TCF mutant according to claim 1, wherein Arg42 of said amino acid sequence of native TCF is mutagenized to Ala.

6. The TCF mutant of SEQ ID NO: 18.

7. The TCF mutant of SEQ ID NO: 19.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 30
      (B) TYPE: NUCLEIC ACID
      (C) STRANDEDNESS: SINGLE
      (D) TOPOLOGY: LINEAR (xi) SEQUENCE DESCRIPTION: SEQ ID NO: 1:

GCCAGCCTGC TGCTCCAGCA TGTCCTCCTG                                        30

(2) INFORMATION FOR SEQ ID NO: 2:

(i) SEQUENCE CHARACTERISTICS:
      (A) LENGTH: 25
      (B) TYPE: NUCLEIC ACID
      (C) STRANDEDNESS: SINGLE
      (D) TOPOLOGY: LINEAR (xi) SEQUENCE DESCRIPTION: SEQ ID NO: 2:

TGCCACTCTT AGTGATAGAT ACTGT                                              25

(2) INFORMATION FOR SEQ ID NO: 3:

(i) SEQUENCE CHARACTERISTICS:
      (A) LENGTH: 34
      (B) TYPE: NUCLEIC ACID
      (C) STRANDEDNESS: SINGLE
      (D) TOPOLOGY: LINEAR (xi) SEQUENCE DESCRIPTION: SEQ ID NO: 3:

TTTTAAAAGG AAGTCCTTTA TTCCTAGTAC ATCT                                  34

(2) INFORMATION FOR SEQ ID NO: 4:

(i) SEQUENCE CHARACTERISTICS:
      (A) LENGTH: 32
      (B) TYPE: NUCLEIC ACID
      (C) STRANDEDNESS: SINGLE (D) TOPOLOGY: LINEAR (xi) SEQUENCE DESCRIPTION: SEQ ID NO: 4:

GGTCGACTAG GCACTGACTC CGAACAGGAT TC                                32

(2) INFORMATION FOR SEQ ID NO: 5:

(i) SEQUENCE CHARACTERISTICS:
        (A) LENGTH: 32
        (B) TYPE: NUCLEIC ACID
        (C) STRANDEDNESS: SINGLE
        (D) TOPOLOGY: LINEAR (xi) SEQUENCE DESCRIPTION: SEQ ID NO: 5:

CCCTATGCAG AGGACAAGCG GCAGCTGCCA TT                                32

(2) INFORMATION FOR SEQ ID NO: 6:

(i) SEQUENCE CHARACTERISTICS:
        (A) LENGTH: 23
        (B) TYPE: NUCLEIC ACID
        (C) STRANDEDNESS: SINGLE
        (D) TOPOLOGY: LINEAR (xi) SEQUENCE DESCRIPTION: SEQ ID NO: 6:

ATACCTGAGA ATCCCAACGC TGA                                          23

(2) INFORMATION FOR SEQ ID NO: 7:

(i) SEQUENCE CHARACTERISTICS:
        (A) LENGTH: 33
        (B) TYPE: NUCLEIC ACID
        (C) STRANDEDNESS: SINGLE
        (D) TOPOLOGY: LINEAR (xi) SEQUENCE DESCRIPTION: SEQ ID NO: 7:

GAATTCATGA ATTGTATTGG CAGCTGCCGC TTG                               33

(2) INFORMATION FOR SEQ ID NO: 8:

(i) SEQUENCE CHARACTERISTICS:
        (A) LENGTH: 35
        (B) TYPE: NUCLEIC ACID
        (C) STRANDEDNESS: SINGLE
        (D) TOPOLOGY: LINEAR (xi) SEQUENCE DESCRIPTION: SEQ ID NO: 8:

GGCAATAGCA ACCGCAGCTG TGAATACTGC AGACG                             35

(2) INFORMATION FOR SEQ ID NO: 9:

(i) SEQUENCE CHARACTERISTICS:
        (A) LENGTH: 38
        (B) TYPE: NUCLEIC ACID
        (C) STRANDEDNESS: SINGLE
        (D) TOPOLOGY: LINEAR (xi) SEQUENCE DESCRIPTION: SEQ ID NO: 9:

CAGCTGCGGT TGCTATTGCC AGTGCTGGAT CTATTTTG                          38

(2) INFORMATION FOR SEQ ID NO: 10:

(i) SEQUENCE CHARACTERISTICS:
        (A) LENGTH: 28
        (B) TYPE: NUCLEIC ACID
        (C) STRANDEDNESS: SINGLE
        (D) TOPOLOGY: LINEAR (xi) SEQUENCE DESCRIPTION: SEQ ID NO: 10:

CCATTCACTT GCGCGGCTTT TGTTTTTG                                          28

(2) INFORMATION FOR SEQ ID NO: 11:

(i) SEQUENCE CHARACTERISTICS:
        (A) LENGTH: 28
        (B) TYPE: NUCLEIC ACID
        (C) STRANDEDNESS: SINGLE
        (D) TOPOLOGY: LINEAR (xi) SEQUENCE DESCRIPTION: SEQ ID NO: 11:

CAAAAACAAA AGCCGCGCAA GTGAATGG                                          28

(2) INFORMATION FOR SEQ ID NO: 12:

(i) SEQUENCE CHARACTERISTICS:
        (A) LENGTH: 36
        (B) TYPE: NUCLEIC ACID
        (C) STRANDEDNESS: SINGLE
        (D) TOPOLOGY: LINEAR (xi) SEQUENCE DESCRIPTION: SEQ ID NO: 12:

GAACACAGCT ATGCGGGTGC AGCCCTACAG GAAAAC                                 36

(2) INFORMATION FOR SEQ ID NO: 13:

(i) SEQUENCE CHARACTERISTICS:
        (A) LENGTH: 36
        (B) TYPE: NUCLEIC ACID
        (C) STRANDEDNESS: SINGLE
        (D) TOPOLOGY: LINEAR (xi) SEQUENCE DESCRIPTION: SEQ ID NO: 13:

GTTTTCCTGT AGGGCTGCAC CCGCATAGCT GTGTTC                                 36

(2) INFORMATION FOR SEQ ID NO: 14:

(i) SEQUENCE CHARACTERISTICS:
        (A) LENGTH: 26
        (B) TYPE: NUCLEIC ACID
        (C) STRANDEDNESS: SINGLE
        (D) TOPOLOGY: LINEAR (xi) SEQUENCE DESCRIPTION: SEQ ID NO: 14:

GAAAACTACT GTGCAAATCC TCGAGG                                            26

(2) INFORMATION FOR SEQ ID NO: 15:

(i) SEQUENCE CHARACTERISTICS:
        (A) LENGTH: 26
        (B) TYPE: NUCLEIC ACID
        (C) STRANDEDNESS: SINGLE
        (D) TOPOLOGY: LINEAR (xi) SEQUENCE DESCRIPTION: SEQ ID NO: 15:

CCTCGAGGAT TTGCACAGTA GTTTTC                                            26

(2) INFORMATION FOR SEQ ID NO: 16:

(i) SEQUENCE CHARACTERISTICS:
        (A) LENGTH: 27
        (B) TYPE: NUCLEIC ACID
        (C) STRANDEDNESS: SINGLE
        (D) TOPOLOGY: LINEAR (xi) SEQUENCE DESCRIPTION: SEQ ID NO: 16:

CAATGTGCTA ATGCATGTAC TAGGAAT                                              27

(2) INFORMATION FOR SEQ ID NO: 17:

(i) SEQUENCE CHARACTERISTICS:
        (A) LENGTH: 26
        (B) TYPE: NUCLEIC ACID
        (C) STRANDEDNESS: SINGLE
        (D) TOPOLOGY: LINEAR (xi) SEQUENCE DESCRIPTION: SEQ ID NO: 17:

ATTCCTAGTA CATGCATAGC ACATTG                                               26

(2) INFORMATION FOR SEQ ID NO: 18:

(i) SEQUENCE CHARACTERISTICS:
        (A) LENGTH: 723
        (B) TYPE: AMINO ACID
        (C) STRANDEDNESS: SINGLE
        (D) TOPOLOGY: LINEAR (xi) SEQUENCE DESCRIPTION: SEQ ID NO: 18:

```
Met Trp Val Thr Lys Leu Leu Pro Ala Leu Leu Leu Gln His Val Leu
    -30              -25              -20

Leu His Leu Leu Leu Leu Pro Ile Ala Ile Pro Tyr Ala Glu Gly Gln
-15              -10               -5              -1   1

Ala Ala Ala Ala Asn Thr Ile His Glu Phe Lys Lys Ser Ala Lys Thr
             5                  10              15

Thr Leu Ile Lys Ile Asp Pro Ala Leu Lys Ile Lys Thr Lys Lys Val
         20              25              30

Asn Thr Ala Asp Gln Cys Ala Asn Arg Cys Thr Arg Asn Lys Gly Leu
     35              40              45

Pro Phe Thr Cys Lys Ala Phe Val Phe Asp Lys Ala Arg Lys Gln Cys
50              55              60              65

Leu Trp Phe Pro Phe Asn Ser Met Ser Ser Gly Val Lys Lys Glu Phe
             70              75              80

Gly His Glu Phe Asp Leu Tyr Glu Asn Lys Asp Tyr Ile Arg Asn Cys
             85              90              95

Ile Ile Gly Lys Gly Arg Ser Tyr Lys Gly Thr Val Ser Ile Thr Lys
        100             105             110

Ser Gly Ile Lys Cys Gln Pro Trp Ser Ser Met Ile Pro His Glu His
        115             120             125

Ser Tyr Arg Gly Lys Asp Leu Gln Glu Asn Tyr Cys Arg Asn Pro Arg
130             135             140             145

Gly Glu Glu Gly Gly Pro Trp Cys Phe Thr Ser Asn Pro Glu Val Arg
            150             155             160

Tyr Glu Val Cys Asp Ile Pro Gln Cys Ser Glu Val Glu Cys Met Thr
            165             170             175

Cys Asn Gly Glu Ser Tyr Arg Gly Leu Met Asp His Thr Glu Ser Gly
            180             185             190

Lys Ile Cys Gln Arg Trp Asp His Gln Thr Pro His Arg His Lys Phe
    195             200             205

Leu Pro Glu Arg Tyr Pro Asp Lys Gly Phe Asp Asp Asn Tyr Cys Arg
210             215             220             225

Asn Pro Asp Gly Gln Pro Arg Pro Trp Cys Tyr Thr Leu Asp Pro His
            230             235             240
```

-continued

```
Thr Arg Trp Glu Tyr Cys Ala Ile Lys Thr Cys Ala Asp Asn Thr Met
            245                 250                 255

Asn Asp Thr Asp Val Pro Leu Glu Thr Thr Glu Cys Ile Gln Gly Gln
            260                 265                 270

Gly Glu Gly Tyr Arg Gly Thr Val Asn Thr Ile Trp Asn Gly Ile Pro
            275                 280                 285

Cys Gln Arg Trp Asp Ser Gln Tyr Pro His Glu His Asp Met Thr Pro
290                 295                 300                 305

Glu Asn Phe Lys Cys Lys Asp Leu Arg Glu Asn Tyr Cys Arg Asn Pro
                310                 315                 320

Asp Gly Ser Glu Ser Pro Trp Cys Phe Thr Thr Asp Pro Asn Ile Arg
                325                 330                 335

Val Gly Tyr Cys Ser Gln Ile Pro Asn Cys Asp Met Ser His Gly Gln
                340                 345                 350

Asp Cys Tyr Arg Gly Asn Gly Lys Asn Tyr Met Gly Asn Leu Ser Gln
            355                 360                 365

Thr Arg Ser Gly Leu Thr Cys Ser Met Trp Asp Lys Asn Met Glu Asp
370                 375                 380                 385

Leu His Arg His Ile Phe Trp Glu Pro Asp Ala Ser Lys Leu Asn Glu
                390                 395                 400

Asn Tyr Cys Arg Asn Pro Asp Asp Asp Ala His Gly Pro Trp Cys Tyr
                405                 410                 415

Thr Gly Asn Pro Leu Ile Pro Trp Asp Tyr Cys Pro Ile Ser Arg Cys
                420                 425                 430

Glu Gly Asp Thr Thr Pro Thr Ile Val Asn Leu Asp His Pro Val Ile
            435                 440                 445

Ser Cys Ala Lys Thr Lys Gln Leu Arg Val Val Asn Gly Ile Pro Thr
450                 455                 460                 465

Arg Thr Asn Ile Gly Trp Met Val Ser Leu Arg Tyr Arg Asn Lys His
                470                 475                 480

Ile Cys Gly Gly Ser Leu Ile Lys Glu Ser Trp Val Leu Thr Ala Arg
                485                 490                 495

Gln Cys Phe Pro Ser Arg Asp Leu Lys Asp Tyr Glu Ala Trp Leu Gly
            500                 505                 510

Ile His Asp Val His Gly Arg Gly Asp Glu Lys Cys Lys Gln Val Leu
    515                 520                 525

Asn Val Ser Gln Leu Val Tyr Gly Pro Glu Gly Ser Asp Leu Val Leu
530                 535                 540                 545

Met Lys Leu Ala Arg Pro Ala Val Leu Asp Asp Phe Val Ser Thr Ile
                550                 555                 560

Asp Leu Pro Asn Tyr Gly Cys Thr Ile Pro Glu Cys Thr Ser Cys Ser
                565                 570                 575

Val Tyr Gly Trp Gly Tyr Thr Gly Leu Ile Asn Tyr Asp Gly Leu Leu
            580                 585                 590

Arg Val Ala His Leu Tyr Ile Met Gly Asn Glu Lys Cys Ser Gln His
    595                 600                 605

His Arg Gly Lys Val Thr Leu Asn Glu Ser Glu Ile Cys Ala Gly Ala
610                 615                 620                 625

Glu Lys Ile Gly Ser Gly Pro Cys Glu Gly Asp Tyr Gly Gly Pro Leu
                630                 635                 640

Val Cys Glu Gln His Lys Met Arg Met Val Leu Gly Val Ile Val Pro
                645                 650                 655

Gly Arg Gly Cys Ala Ile Pro Asn Arg Pro Gly Ile Phe Val Arg Val
```

-continued

```
              660                 665                 670
Ala Tyr Tyr Ala Lys Trp Ile His Lys Ile I le Leu Thr Tyr Lys Val
    675                 680                 685

Pro Gln Ser
690
```

(2) INFORMATION FOR SEQ ID NO: 19:

(i) SEQUENCE CHARACTERISTICS:
        (A) LENGTH: 723
        (B) TYPE: AMINO ACID
        (C) STRANDEDNESS: SINGLE
        (D) TOPOLOGY: LINEAR (xi) SEQUENCE DESCRIPTION: SEQ ID NO: 19:

```
Met Trp Val Thr Lys Leu Leu Pro Ala Leu L eu Leu Gln His Val Leu
    -30                 -25                 -20

Leu His Leu Leu Leu Leu Pro Ile Ala Ile P ro Tyr Ala Glu Gly Gln
    -15                 -10                 -5             -1   1

Arg Lys Arg Arg Asn Thr Ile His Glu Phe L ys Lys Ser Ala Lys Thr
                5                   10                  15

Thr Leu Ile Lys Ile Asp Pro Ala Leu Ala I le Ala Thr Ala Ala Val
                20                  25                  30

Asn Thr Ala Asp Gln Cys Ala Asn Arg Cys T hr Arg Asn Lys Gly Leu
        35                  40                  45

Pro Phe Thr Cys Lys Ala Phe Val Phe Asp L ys Ala Arg Lys Gln Cys
50                  55                  60                  65

Leu Trp Phe Pro Phe Asn Ser Met Ser Ser G ly Val Lys Lys Glu Phe
                    70                  75                  80

Gly His Glu Phe Asp Leu Tyr Glu Asn Lys A sp Tyr Ile Arg Asn Cys
                85                  90                  95

Ile Ile Gly Lys Gly Arg Ser Tyr Lys Gly T hr Val Ser Ile Thr Lys
                100                 105                 110

Ser Gly Ile Lys Cys Gln Pro Trp Ser Ser M et Ile Pro His Glu His
    115                 120                 125

Ser Tyr Arg Gly Lys Asp Leu Gln Glu Asn T yr Cys Arg Asn Pro Arg
130                 135                 140                 145

Gly Glu Glu Gly Gly Pro Trp Cys Phe Thr S er Asn Pro Glu Val Arg
                    150                 155                 160

Tyr Glu Val Cys Asp Ile Pro Gln Cys Ser G lu Val Glu Cys Met Thr
                165                 170                 175

Cys Asn Gly Glu Ser Tyr Arg Gly Leu Met A sp His Thr Glu Ser Gly
        180                 185                 190

Lys Ile Cys Gln Arg Trp Asp His Gln Thr P ro His Arg His Lys Phe
    195                 200                 205

Leu Pro Glu Arg Tyr Pro Asp Lys Gly Phe A sp Asp Asn Tyr Cys Arg
210                 215                 220                 225

Asn Pro Asp Gly Gln Pro Arg Pro Trp Cys T yr Thr Leu Asp Pro His
                    230                 235                 240

Thr Arg Trp Glu Tyr Cys Ala Ile Lys Thr C ys Ala Asp Asn Thr Met
                245                 250                 255

Asn Asp Thr Asp Val Pro Leu Glu Thr Thr G lu Cys Ile Gln Gly Gln
        260                 265                 270

Gly Glu Gly Tyr Arg Gly Thr Val Asn Thr I le Trp Asn Gly Ile Pro
    275                 280                 285
```

-continued

```
Cys Gln Arg Trp Asp Ser Gln Tyr Pro His Glu His Asp Met Thr Pro
290                     295                 300                 305

Glu Asn Phe Lys Cys Lys Asp Leu Arg Glu Asn Tyr Cys Arg Asn Pro
            310                 315                 320

Asp Gly Ser Glu Ser Pro Trp Cys Phe Thr Thr Asp Pro Asn Ile Arg
                325                 330                 335

Val Gly Tyr Cys Ser Gln Ile Pro Asn Cys Asp Met Ser His Gly Gln
            340                 345                 350

Asp Cys Tyr Arg Gly Asn Gly Lys Asn Tyr Met Gly Asn Leu Ser Gln
        355                 360                 365

Thr Arg Ser Gly Leu Thr Cys Ser Met Trp Asp Lys Asn Met Glu Asp
370                 375                 380                 385

Leu His Arg His Ile Phe Trp Glu Pro Asp Ala Ser Lys Leu Asn Glu
                390                 395                 400

Asn Tyr Cys Arg Asn Pro Asp Asp Asp Ala His Gly Pro Trp Cys Tyr
            405                 410                 415

Thr Gly Asn Pro Leu Ile Pro Trp Asp Tyr Cys Pro Ile Ser Arg Cys
                420                 425                 430

Glu Gly Asp Thr Thr Pro Thr Ile Val Asn Leu Asp His Pro Val Ile
435                 440                 445

Ser Cys Ala Lys Thr Lys Gln Leu Arg Val Val Asn Gly Ile Pro Thr
450                 455                 460                 465

Arg Thr Asn Ile Gly Trp Met Val Ser Leu Arg Tyr Arg Asn Lys His
                470                 475                 480

Ile Cys Gly Gly Ser Leu Ile Lys Glu Ser Trp Val Leu Thr Ala Arg
            485                 490                 495

Gln Cys Phe Pro Ser Arg Asp Leu Lys Asp Tyr Glu Ala Trp Leu Gly
        500                 505                 510

Ile His Asp Val His Gly Arg Gly Asp Glu Lys Cys Lys Gln Val Leu
515                 520                 525

Asn Val Ser Gln Leu Val Tyr Gly Pro Glu Gly Ser Asp Leu Val Leu
530                 535                 540                 545

Met Lys Leu Ala Arg Pro Ala Val Leu Asp Asp Phe Val Ser Thr Ile
                550                 555                 560

Asp Leu Pro Asn Tyr Gly Cys Thr Ile Pro Glu Lys Thr Ser Cys Ser
            565                 570                 575

Val Tyr Gly Trp Gly Tyr Thr Gly Leu Ile Asn Tyr Asp Gly Leu Leu
        580                 585                 590

Arg Val Ala His Leu Tyr Ile Met Gly Asn Glu Lys Cys Ser Gln His
595                 600                 605

His Arg Gly Lys Val Thr Leu Asn Glu Ser Glu Ile Cys Ala Gly Ala
610                 615                 620                 625

Glu Lys Ile Gly Ser Gly Pro Cys Glu Gly Asp Tyr Gly Gly Pro Leu
                630                 635                 640

Val Cys Glu Gln His Lys Met Arg Met Val Leu Gly Val Ile Val Pro
            645                 650                 655

Gly Arg Gly Cys Ala Ile Pro Asn Arg Pro Gly Ile Phe Val Arg Val
        660                 665                 670

Ala Tyr Tyr Ala Lys Trp Ile His Lys Ile Ile Leu Thr Tyr Lys Val
            675                 680                 685

Pro Glu Ser
690
```

```
(2) INFORMATION FOR SEQ ID NO: 20:

(i) SEQUENCE CHARACTERISTICS:
        (A) LENGTH: 4
        (B) TYPE: AMINO ACID
        (C) STRANDEDNESS: SINGLE
        (D) TOPOLOGY: LINEAR (xi) SEQUENCE DESCRIPTION: SEQ ID NO: 20:

Arg Lys Arg Arg
 1

(2) INFORMATION FOR SEQ ID NO: 21:

(i) SEQUENCE CHARACTERISTICS:
        (A) LENGTH: 4
        (B) TYPE: AMINO ACID
        (C) STRANDEDNESS: SINGLE
        (D) TOPOLOGY: LINEAR (xi) SEQUENCE DESCRIPTION: SEQ ID NO: 21:

Ala Ala Ala Ala
 1

(2) INFORMATION FOR SEQ ID NO: 22:

(i) SEQUENCE CHARACTERISTICS:
        (A) LENGTH: 6
        (B) TYPE: AMINO ACID
        (C) STRANDEDNESS: SINGLE
        (D) TOPOLOGY: LINEAR (xi) SEQUENCE DESCRIPTION: SEQ ID NO: 22:

Lys Ile Lys Thr Lys Lys
 1               5

(2) INFORMATION FOR SEQ ID NO: 23:

(i) SEQUENCE CHARACTERISTICS:
        (A) LENGTH: 6
        (B) TYPE: AMINO ACID
        (C) STRANDEDNESS: SINGLE
        (D) TOPOLOGY: LINEAR (xi) SEQUENCE DESCRIPTION: SEQ ID NO: 23:

Ala Ile Ala Thr Ala Ala
 1               5

(2) INFORMATION FOR SEQ ID NO: 24:

(i) SEQUENCE CHARACTERISTICS:
        (A) LENGTH: 4
        (B) TYPE: AMINO ACID
        (C) STRANDEDNESS: SINGLE
        (D) TOPOLOGY: LINEAR (xi) SEQUENCE DESCRIPTION: SEQ ID NO: 24:

Arg Gly Lys Asp
 1

(2) INFORMATION FOR SEQ ID NO: 25:

(i) SEQUENCE CHARACTERISTICS:
        (A) LENGTH: 4
        (B) TYPE: AMINO ACID
        (C) STRANDEDNESS: SINGLE
        (D) TOPOLOGY: LINEAR (xi) SEQUENCE DESCRIPTION: SEQ ID NO: 25:
```

```
Ala Gly Ala Ala
  1
```